United States Patent
Foster

(10) Patent No.: US 10,660,996 B2
(45) Date of Patent: May 26, 2020

(54) CARDIAC PUMP

(71) Applicant: Calon Cardio-Technology Ltd., Swansea West, Glamorgan (GB)

(72) Inventor: Graham Foster, Glamorgan (GB)

(73) Assignee: Calon Cardio-Technology Ltd., Swansea West, Glamorgan (GB)

( * ) Notice: Subject to any disclaimer, the term of this patent is extended or adjusted under 35 U.S.C. 154(b) by 225 days.

(21) Appl. No.: 15/317,502

(22) PCT Filed: Jun. 9, 2015

(86) PCT No.: PCT/GB2015/051677
§ 371 (c)(1),
(2) Date: Dec. 9, 2016

(87) PCT Pub. No.: WO2015/189590
PCT Pub. Date: Dec. 17, 2015

(65) Prior Publication Data
US 2017/0128644 A1    May 11, 2017

(30) Foreign Application Priority Data
Jun. 10, 2014   (GB) .................................. 1410272.7

(51) Int. Cl.
*A61M 1/10*        (2006.01)
*A61M 1/12*        (2006.01)

(52) U.S. Cl.
CPC ........... *A61M 1/1015* (2014.02); *A61M 1/101* (2013.01); *A61M 1/1012* (2014.02);
(Continued)

(58) Field of Classification Search
CPC ..... A61M 1/101; A61M 1/1031; A61M 1/122
(Continued)

(56) References Cited

U.S. PATENT DOCUMENTS 5,507,629 A    4/1996  Jarvik
5,695,471 A   12/1997  Wampler
(Continued)

FOREIGN PATENT DOCUMENTS

JP       H11123239 A    5/1999

OTHER PUBLICATIONS

Patent Act 1977: Search Report under Section 17(5), Application No. GB1410272.7 dated Jan. 6, 2015.
(Continued)

*Primary Examiner* — Nadia A Mahmood
(74) *Attorney, Agent, or Firm* — MacMillan, Sobanski & Todd, LLC

(57) ABSTRACT

A cardiac pump includes a plain bearing assembly having a first plain bearing portion that is coupled to a cardiac pump rotor and a second lain bearing portion that is coupled to a cardiac pump housing. The plain bearing assembly is configured to rotatably support the cardiac pump rotor within the cardiac pump housing in at least an axial direction of the cardiac pump rotor. A magnetic bearing assembly includes a first magnetic bearing portion that is coupled to the cardiac pump rotor and a second magnetic bearing portion that is coupled to the cardiac pump housing. The magnetic bearing assembly is configured to rotatably support the cardiac pump rotor within the cardiac pump housing in a radial direction of the cardiac pump rotor and bias the cardiac pump rotor in the axial direction such that the magnetic bearing assembly provides a preload force to preload the plain bearing assembly.

21 Claims, 5 Drawing Sheets

(52) U.S. Cl.
CPC ......... *A61M 1/1013* (2014.02); *A61M 1/1031* (2014.02); *A61M 1/122* (2014.02); *A61M 2207/00* (2013.01)

(58) Field of Classification Search
USPC .......................................................... 600/16
See application file for complete search history.

(56) References Cited

U.S. PATENT DOCUMENTS

| | | |
|---|---|---|
| 5,840,070 A | 11/1998 | Wampler |
| 6,120,537 A | 9/2000 | Wampler |
| 6,234,772 B1 | 5/2001 | Wampler et al. |
| 6,254,359 B1 | 7/2001 | Aber |
| 6,255,752 B1 | 7/2001 | Werner |
| 2003/0135086 A1* | 7/2003 | Khaw ................. A61M 1/1024 600/16 |
| 2008/0310963 A1 | 12/2008 | Wampler et al. |
| 2012/0245404 A1 | 9/2012 | Smith et al. |
| 2014/0046118 A1* | 2/2014 | LaRose ................ A61M 1/101 600/16 |

OTHER PUBLICATIONS

International Search Report and the Written Opinion, Application No. PCT/GB20151051677 filed Jun. 9, 2015, dated Sep. 14, 2015.
PCT Written Opinion, Application No. PCT/GB2015/051677, dated Sep. 14, 2015.
Japanese Office Action, Application No. 2016-572278, dated Mar. 26, 2019.

* cited by examiner

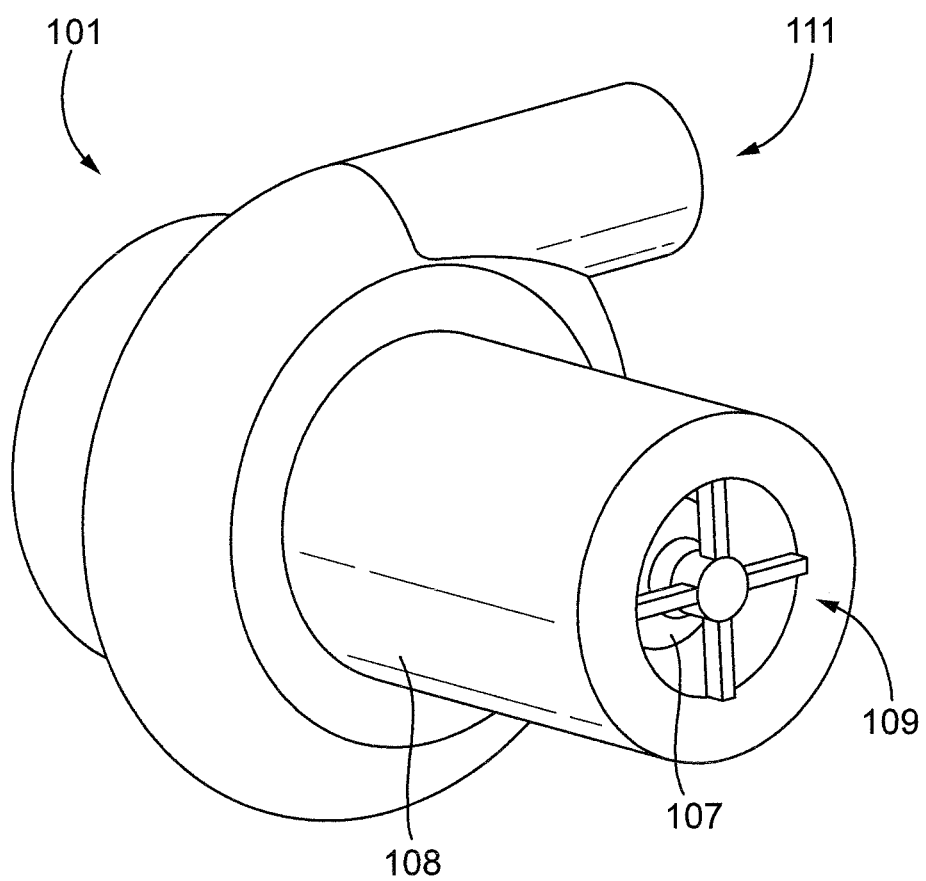

CARDIAC PUMP

CROSS-REFERENCE TO RELATED APPLICATIONS

This application is the National Phase of International Application PCT/GB2015/051677 filed Jun. 9, 2015, which designated the U.S. That International Application was published in English under PCT Article 21(2) on Dec. 17, 2015 as International Publication Number WO 2015/189590A1. PCT/GB2015/051677 claims priority to U.K. Patent Application No. 1410272.7 filed Jun. 10, 2014. Thus, the subject nonprovisional application also claims priority to U.K. Patent Application No. 1410272.7. The disclosures of both applications are incorporated herein by reference.

This disclosure relates to a cardiac pump having a plain bearing assembly and a magnetic bearing assembly and particularly, but not exclusively, relates to a cardiac pump comprising a plain bearing assembly configured to support a cardiac pump rotor, and a magnetic bearing assembly configured to support the cardiac pump rotor and provide a preload force to preload the plain bearing assembly.

BACKGROUND

Advanced heart failure is a major global health problem resulting in many thousands of deaths each year and those with the disease endure a very poor quality of life. The treatment options for advanced heart failure, for example drug therapy and cardiac resynchronization (pacemakers), have generally proved unsuccessful and the only option remaining for the patients is heart transplantation. Unfortunately, the number of donor hearts available only meets a fraction of the demand, leaving many people untreated.

Ventricular Assist Devices (VAD) have been gaining increased acceptance over the last decade as an alternative therapy to heart transplantation. The use of VADs has shown that, in most cases, once the device has been implanted, the disease progression is halted, the symptoms of heart failure are relieved, and the patient regains a good quality of life.

VADs can be considered as a viable alternative to treat heart failure and offer hope to the many thousands of heart failure patients for whom a donor heart will not be available.

In general terms, it is known to provide a cardiac pump, such as a VAD, that is suitable for implantation into a ventricle of a human heart. The most common type of these implantable pumps is a miniaturised rotary pump, due to their small size and mechanical simplicity/reliability. Such known devices have two primary components: a cardiac pump housing, which defines a cardiac pump inlet and a cardiac pump outlet; and a cardiac pump rotor, which is housed within the cardiac pump housing, and which is configured to impart energy to the fluid.

A requirement for the cardiac pump, therefore, is a bearing system that rotatably supports the cardiac pump rotor within the cardiac pump housing. Bearings systems for cardiac pumps, and generally all rotating machines such as pumps and motors, ideally achieve the fundamental function of permitting rotation of a the rotor, whilst providing sufficient constraint to the rotor in all other degrees of freedom, i.e. the bearing system must support the rotor axially, radially and in pitch/yaw.

Desirable functions of bearing systems generally may include low rates of wear and low noise and vibration, and the case of blood pumps, elimination of features that trap blood, or introduce shear stress or heat in the blood.

In known devices, the cardiac pump rotor may be rotatably supported within the housing using one of a number of different types of bearing systems. In general, there are three types of bearing systems that are utilised in cardiac pumps.

Some cardiac pumps use blood-immersed contact bearings, for example a pair of plain bearings, to rigidly support the rotor within the housing. However, for such plain bearing systems it may be difficult to ensure that the rotor is perfectly entrapped within the contact bearings. Moreover, blood-immersed contact bearings of the prior art may be susceptible to proteinacious and other biological deposition in the bearings, and also the region proximate to and supporting structures around the contact bearings.

Other cardiac pumps use non-contact hydrodynamic bearing systems, in which the rotor is supported on a thin film of blood. In order to produce the required levels hydrodynamic lift, hydrodynamic bearing systems require small running clearances. As a consequence, blood that passes through those small running clearances may be subjected to high levels of shear stress, which may have a detrimental effect on the cellular components of the blood, for example by causing haemolysis or platelet activation which may further lead to thrombosis.

Cardiac pumps may also employ non-contact magnetic bearing systems, in which the running clearances between the rotor and the housing may be designed such that large gaps can exist in the bearing and therefore shear-related blood damage in the bearing is reduced. However, due to the limitations resulting from Earnshaw's theorem, a passive magnetic bearing system requires another manner of support in at least one degree-of-freedom, for example active magnetic control, which may significantly increase the size and complexity of the design, and/or hydrodynamic suspension, which may increase the requirements with regard to manufacturing tolerances or introduce blood damage.

STATEMENTS OF INVENTION

According to an aspect of the present disclosure there is provided a cardiac pump comprising a plain bearing assembly having a first plain bearing portion and a second plain bearing portion. The first plain bearing portion is coupled to a cardiac pump rotor and the second plain bearing portion is coupled to a cardiac pump housing. The plain bearing assembly is configured to support, e.g. rotatably support, the cardiac pump rotor within the cardiac pump housing in at least an axial direction of the cardiac pump rotor. The cardiac pump comprises a magnetic bearing assembly having a first magnetic bearing portion and a second magnetic bearing portion. The first magnetic bearing portion is coupled, e.g. movably coupled, to the cardiac pump rotor and the second magnetic bearing portion is coupled, e.g. movably coupled, to the cardiac pump housing. The magnetic bearing assembly is configured to support, e.g. rotatably support, the cardiac pump rotor within the cardiac pump housing in a radial direction of the cardiac pump rotor.

Together the plain bearing assembly and the magnetic bearing assembly create a bearing system that achieves the fundamental requirement of a bearing system for a rotation machine by supporting the rotor axially, radially and in pitch/yaw, whilst permitting the rotation of the rotor.

The magnetic bearing assembly may be configured to bias the cardiac pump rotor in the axial direction. The magnetic bearing assembly is configured to provide a preload force to preload the plain bearing assembly. The plain bearing assembly may be configured to support the cardiac pump rotor in the radial direction. The plain bearing assembly may be configured to support the rotor in the axial direction and to permit free movement of the cardiac pump rotor in the radial direction.

The first magnetic bearing portion may be movably coupled, for example slidably and/or rotationally coupled, to the cardiac pump rotor when the cardiac pump is in an assembled configuration. The second magnetic bearing portion may be movably coupled, for example slidably and/or rotationally coupled, to the cardiac pump housing when the cardiac pump is in an assembled configuration. In the context of the present disclosure, the term "assembled configuration", when applied to the cardiac pump, may be interpreted as a configuration in which the cardiac pump rotor is assembled into at least a portion of the cardiac pump housing. Additionally or alternatively, the second magnetic bearing portion may be movably coupled to the cardiac pump housing when the cardiac pump is in an operable configuration. In the context of the present disclosure, the term "operable configuration", when applied to the cardiac pump, may be interpreted as a configuration in which the cardiac pump is fully assembled and ready to be switched on, i.e. ready to pump a fluid, or operating.

The position of the first and/or second magnetic bearing portion may be adjustable relative to the cardiac pump rotor and/or the cardiac pump housing. For example, the position of the first and/or second magnetic bearing portion may be adjustable when the cardiac pump is in an assembled configuration. The magnitude of the preload force may be dependent upon the position of the first and/or second magnetic bearing portion when the cardiac pump housing and the cardiac pump rotor are in an assembled configuration. The magnitude of the preload force may be adjusted, for example set to a required level, by adjusting the position of the first and/or second magnetic bearing portion when the cardiac pump is in an assembled configuration. The position of the second magnetic bearing portion may be adjusted, for example set to a required position, when the cardiac pump is an operable configuration. In this manner, the magnitude of the preload force may be adjusted, for example set to a required level, when the cardiac pump is operating.

The cardiac pump rotor may comprise a magnetic bearing engagement portion, for example a bore, opening, recess or projection, configured to receive the first magnetic bearing portion. The magnetic bearing engagement portion of the cardiac pump rotor may allow the position of first magnetic bearing portion to be adjusted through a range of positions. The range of positions may be defined by the extent by which the first magnetic bearing portion may be moved within, over and/or around the magnetic bearing engagement portion of the cardiac pump rotor. For example, when the first magnetic bearing portion is moved towards one end of the range of positions, the preload force may be reduced, and when the first magnetic bearing portion is moved towards the other end of the range of positions, the preload force may be increased.

The cardiac pump housing may comprise a magnetic bearing engagement portion, for example a bore, opening, recess or projection, configured to receive the second magnetic bearing portion. The magnetic bearing engagement portion of the cardiac pump housing may allow the position of second magnetic bearing portion to be adjusted through a range of positions. The range of positions may be defined by the extent by which the second magnetic bearing portion may be moved within, over and/or around the magnetic bearing engagement portion of the cardiac pump housing. For example, when the second magnetic bearing portion is moved towards one end of the range of positions, the preload force may be reduced, and when the second magnetic bearing portion is moved towards the other end of the range of positions, the preload force may be increased.

The first and/or second magnetic bearing portion may be threadably adjustable. The position of the first and/or the second magnetic bearing portion may be adjustable in the axial and/or the radial direction, for example relative to a longitudinal axis of the cardiac pump rotor.

The position of the first and/or second plain bearing portion may be adjustable relative to the cardiac pump rotor and/or the cardiac pump housing. The magnitude of the preload force may be dependent upon the position of the first and/or second plain bearing portion when the cardiac pump housing and the cardiac pump rotor are in an assembled configuration. The first and/or second plain bearing portion may be threadably adjustable. The position of the first and/or the second plain bearing portion may be adjustable in the axial and/or the radial direction, for example relative to a longitudinal axis of the cardiac pump rotor.

The cardiac pump may comprise a magnetic bearing assembly adjuster configured to adjust the position of the first and/or second magnetic bearing portion. The magnetic bearing assembly adjuster may be configured to couple, for example slidably and/or rotationally couple, the first magnetic bearing portion to the cardiac pump rotor. The magnetic bearing assembly adjuster may be configured to couple, for example slidably and/or rotationally couple, the second magnetic bearing portion to the cardiac pump housing.

The cardiac pump may comprise a further magnetic bearing assembly. The further magnetic bearing assembly may comprise a first further magnetic bearing portion and a second further magnetic bearing portion. The magnetic bearing assembly and the further magnetic bearing assembly may be spaced apart from each other in at least the axial direction. The magnetic bearing assembly and the further magnetic bearing assembly may be spaced apart from each other in the radial direction. The further magnetic bearing assembly may be configured to at least partially support the cardiac pump rotor within the cardiac pump housing in the axial direction and/or the radial direction. The further magnetic bearing assembly may be configured to bias the cardiac pump rotor in the axial direction and/or the radial direction, for example in a direction towards or away from the plain bearing assembly, the magnetic bearing assembly and/or a portion of the cardiac pump housing. The magnetic bearing assembly and the further magnetic bearing assembly may be axially spaced apart from each other, such that the combination of the magnetic bearing assembly and the further magnetic bearing assembly provides support for the cardiac pump rotor in pitch and/or yaw.

The cardiac pump may comprise a magnetic drive coupling. The cardiac pump rotor may comprise a first portion of the magnetic drive coupling. The cardiac pump housing may comprise a second portion of the magnetic drive coupling. The first and second portions of the magnetic drive coupling may be at least partially disposed in between, e.g. axially and/or radially in between, the magnetic bearing assembly and the further magnetic bearing assembly.

The cardiac pump rotor may comprise an impeller portion. The impeller portion may be at least partially disposed in between, e.g. axially and/or radially in between, the magnetic bearing assembly and the further magnetic bearing assembly.

The cardiac pump may comprise a further plain bearing assembly. The further plain bearing assembly may comprise a first further plain bearing portion and a second further plain bearing portion. The plain bearing assembly and the further plain bearing assembly may be spaced apart from each other in at least the axial direction. The plain bearing assembly and the further plain bearing assembly may be spaced apart from each other in the radial direction. The further plain bearing assembly may be configured to limit a range of movement of the cardiac pump rotor within the cardiac pump housing in a direction opposite to the direction of the preload force.

The cardiac pump may be configured such that, during operation, the first and second plain bearing portions of the plain bearing assembly are in rotatable contact. The cardiac pump may be configured such that, during operation and the first and second plain bearing portions of the further plain bearing assembly have an operational clearance between each other. The cardiac pump may be configured such that, during operation, the first and second plain bearing portions of the further plain bearing assembly are in rotatable contact. The cardiac pump may be configured such that, during operation and the first and second plain bearing portions of the plain bearing assembly have an operational clearance between each other.

The cardiac pump may comprise a primary flow path configured to connect fluidically a cardiac pump inlet and a cardiac pump outlet. The cardiac pump may comprise one or more secondary flow paths at least partially configured to connect fluidically two or more regions of the primary flow path.

The plain bearing assembly may be at least partially disposed within the primary flow path. The further plain bearing assembly may be at least partially disposed within the primary flow path. The plain bearing assembly may be at least partially disposed within the secondary flow path. The further plain bearing assembly may be at least partially disposed within the secondary flow path. The operational clearance between the first and second plain bearing portions of the plain bearing assembly may be at least partially disposed in the primary flow path. The operational clearance between the first and second plain bearing portions of the plain bearing assembly may be at least partially disposed in the secondary flow path. The operational clearance between the first and second plain bearing portions of the further plain bearing assembly may be at least partially disposed in the primary flow path. The operational clearance between the first and second plain bearing portions of the further plain bearing assembly may be at least partially disposed in the secondary flow path.

According to a second aspect of the present disclosure there is provided a method of preloading a plain bearing assembly of a cardiac pump, the cardiac pump comprising the plain bearing assembly and a magnetic bearing assembly. The plain bearing assembly comprises a first plain bearing portion and a second plain bearing portion. The first plain bearing portion is coupled to a cardiac pump rotor. The second plain bearing portion is coupled to a cardiac pump housing. The plain bearing assembly is configured to support, e.g. rotatably support, the cardiac pump rotor within the cardiac pump housing in at least an axial direction of the cardiac pump rotor. The magnetic bearing assembly comprises a first magnetic bearing portion and a second magnetic bearing portion. The first magnetic bearing portion is coupled, e.g. movably coupled, to the cardiac pump rotor and a second magnetic bearing portion being coupled, e.g. movably coupled, to the cardiac pump housing. The magnetic bearing assembly is configured to support, e.g. rotatably support, the cardiac pump rotor within the cardiac pump housing in a radial direction of the cardiac pump rotor and the axial direction. The magnetic bearing assembly is configured to provide a preload force to preload the plain bearing assembly when the cardiac pump housing and the cardiac pump rotor are in an assembled configuration. The method comprises preloading the plain bearing assembly with the preload force provided by the magnetic bearing assembly.

The magnitude of the preload force may be dependent upon the position of the first and/or the second magnetic bearing portion relative to the cardiac pump rotor and/or the cardiac pump housing when the cardiac pump housing and the cardiac pump rotor are in an assembled configuration. The method may further comprise adjusting the position of the first and/or the second magnetic bearing portion relative to the cardiac pump rotor and/or the cardiac pump housing when the cardiac pump housing and the cardiac pump rotor are in an assembled configuration.

BRIEF DESCRIPTION OF THE DRAWINGS

For a better understanding of the present disclosure, and to show more clearly how it may be carried into effect, reference will now be made, by way of example, to the accompanying drawings, in which:

FIG. 2a shows an isometric view of an example of a cardiac pump according to the present disclosure in an assembled configuration;

DETAILED DESCRIPTION

Figure 1:
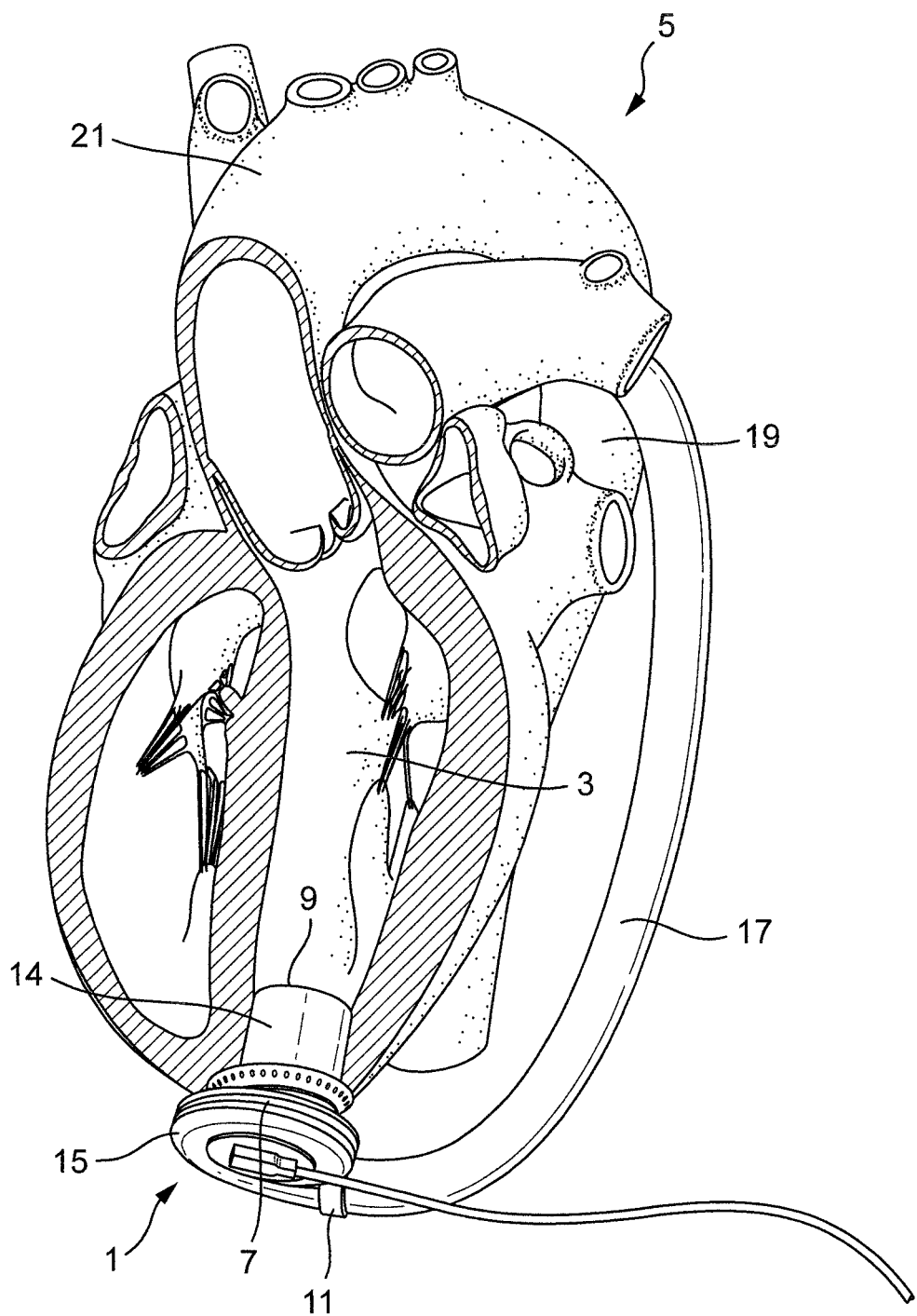
FIG. 1 shows a cut-away of a heart with a cardiac pump implanted into the left ventricle.

FIG. 1 depicts a cardiac pump 1 for the treatment of heart failure, for example a Ventricular Assist Device (VAD), in an implanted configuration in the left ventricle 3 of a heart 5. The cardiac pump 1 comprises a cardiac pump housing 7 comprising an inlet 9 for blood and an outlet 11 for blood. The cardiac pump 1 comprises a cardiac pump rotor disposed at least partially within the cardiac pump housing 7. The cardiac pump rotor is supported, for example rotatably supported, by way of one or more bearing assemblies, as described below.

The cardiac pump 1 comprises an inflow cannula 14 situated at least partially inside the left ventricle 3 and a pumping chamber 15 situated outside of the heart 5. The inflow cannula 14 extends between the pumping chamber 15, through the wall of the left ventricle 3 into the chamber of the left ventricle 3, so that the inlet 9 is situated completely within the left ventricle 3. The pumping chamber 15 is situated on the apex of the left ventricle 3 with the outlet 11 connected to an outflow cannula 17. In the example shown in FIG. 1, the outflow cannula 17 is anastomosed to a descending aorta 19, although in an alternative example the outflow cannula 17 may be anastomosed to an ascending aorta 21.

The present disclosure relates to a cardiac pump 1 that reduces the risk of damage to the cellular components of the blood, and which simplifies the manufacture and assembly of the cardiac pump 1. For example, the cardiac pump 1 according to the present disclosure may mitigate the deposition of proteins and/or the formation of thrombi within the cardiac pump 1, and in particular, may mitigate the deposition of proteins and/or the formation of thrombi in areas proximate to bearing assemblies. In the examples described below, the cardiac pump 1 comprises a plain bearing assembly and a magnetic bearing assembly. The cardiac pump 1 may, however, comprise one or more further plain bearing assemblies and one or more further magnetic bearing assemblies.

The plain bearing assembly is a type of contact bearing assembly in which the bearing surfaces of the plain bearing assembly are configured to be in contact during operation of the cardiac pump 1. For example, the plain bearing assembly may comprise no intermediate rolling elements, i.e. motion is transmitted directly between two or more contacted surfaces of respective portions of the plain bearing assembly.

The magnetic bearing assembly is a type of non-contact bearing assembly in which the cardiac pump rotor is supported by virtue of the interaction between the magnetic fields of the respective portions of the magnetic bearing assembly. For example, the magnetic bearing assembly may comprise a combination of permanent magnets configured to support the cardiac pump rotor within the cardiac pump housing by virtue of the attractive and/or repulsive forces between the respective portions of the magnetic bearing assembly. It is appreciated, however, that in an alternative example the magnetic bearing assembly may comprise a combination of permanent magnets and/or electro magnets configured to support the cardiac pump rotor.

Figure 2B:
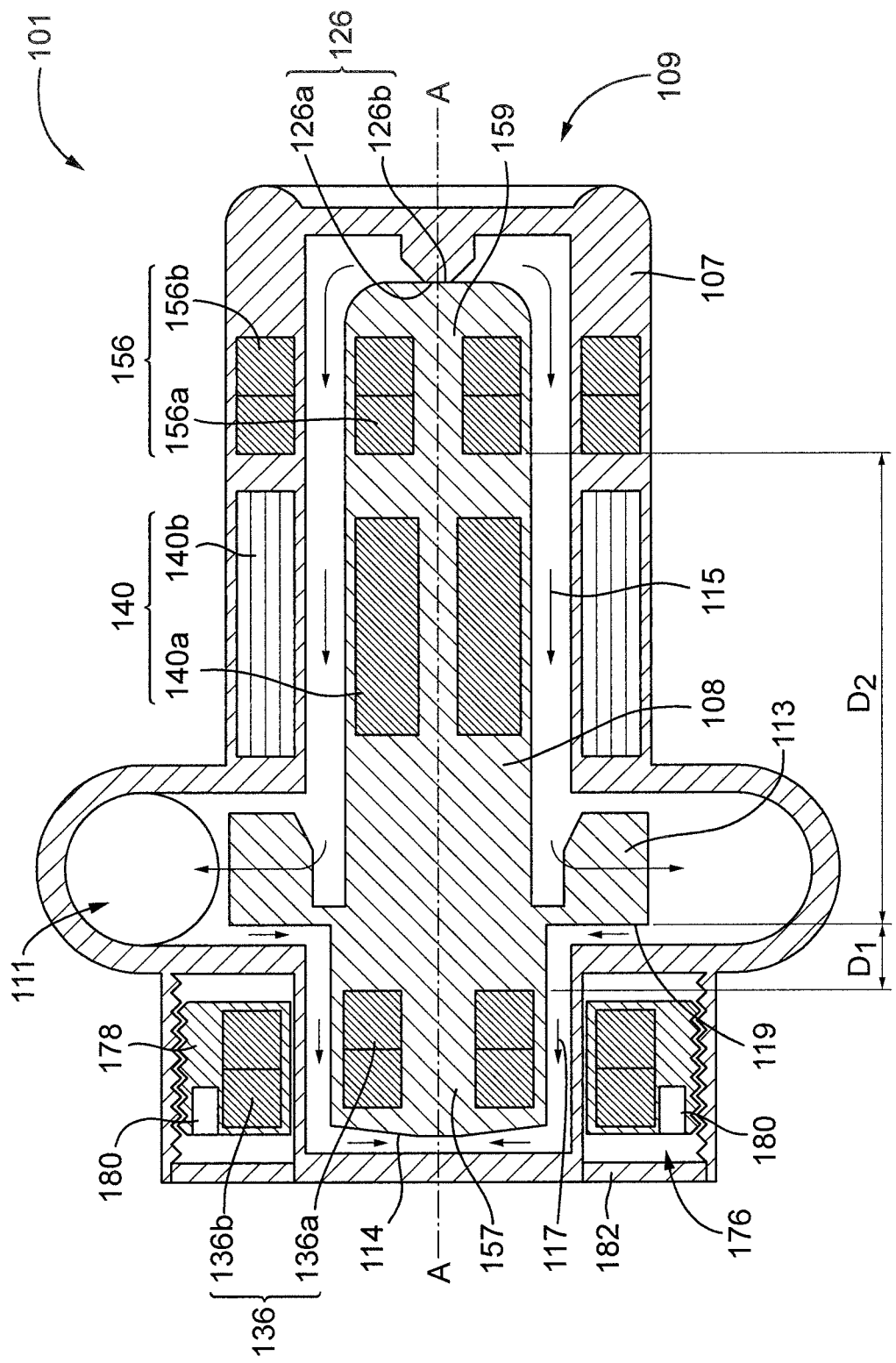
FIG. 2b shows a cross sectional view of the example of the cardiac pump according to the present disclosure in an assembled configuration.

FIG. 2a shows an example of a cardiac pump 101 and FIG. 2b shows a cross-section through the cardiac pump 101 along a longitudinal axis A-A. The cardiac pump 101 comprises a primary flow path 115, which is defined as the flow of blood between the inlet 109 and the outlet 111 of the cardiac pump 101. The cardiac pump 101 may further comprise a secondary flow path 117, which is defined as any recirculating flow inside the cardiac pump 1 that does not form part of the primary flow path 115. The secondary flow path 117 may be configured to at least partially fluidically connect two or more regions of the primary flow path 115.

The cardiac pump 101 comprises a cardiac pump housing 107 and a cardiac pump rotor 108. The cardiac pump rotor 108 is rotatably coupled to an impeller portion 113 configured to pump the blood and which may be provided at or towards an end of the cardiac pump rotor 108. In the example shown in FIG. 2b, the cardiac pump rotor 108 is supported by a bearing system that comprises the plain bearing assembly 126, the magnetic bearing assembly 136 and the further magnetic bearing assembly 156, such that the cardiac pump rotor 108 is substantially constrained, e.g. in five degrees-of-freedom, and the cardiac pump rotor 108 may rotate about the longitudinal axis A-A. The bearing system of the cardiac pump 101 permits rotation of the cardiac pump rotor 108, which is a fundamental function of the bearing system, and provides sufficient constraint to the cardiac pump rotor 108 in all other degrees of freedom. In this manner, the bearing system supports the cardiac pump rotor 108 in the axial and radial directions, as well as in pitch and yaw.

In the example shown in FIG. 2b, the plain bearing assembly 126 and the further magnetic bearing assembly 156 are located towards the inlet 109 of the cardiac pump 101, and the magnetic bearing assembly 136 is located towards the outlet end 111 of the cardiac pump 101. It is appreciated, however, that any of the bearing assemblies of the cardiac pump 101 may be positioned at any appropriate portion of the cardiac pump 101, dependent upon the operational requirements of the cardiac pump 101.

The plain bearing assembly 126 comprises a first plain bearing portion 126a. The first plain bearing portion 126a is coupled to the cardiac pump rotor 108 such that, during operation of the cardiac pump 101, the first plain bearing portion 126a rotates with the cardiac pump rotor 108. In the example shown in FIG. 2b, the first plain bearing portion 126a is integral to the cardiac pump rotor 108, although in an alternative example the first plain bearing portion 126a may be a separate component rigidly fixed to the cardiac pump rotor 108. In another example, the first plain bearing portion 126a may be movably coupled, for example threadably coupled, to the cardiac pump rotor 108 such that the position of the first plain bearing portion 126a may be adjusted relative to the cardiac pump rotor 108. The first plain bearing portion 126a may be constructed from a different material to the cardiac pump rotor 108, e.g. a ceramic material. Alternatively, the first plain bearing portion 126a may be constructed from a similar material to the cardiac pump rotor 108, e.g. a titanium alloy. The first plain bearing portion 126a may comprise a surface coating and/or may have had a surface treatment to improve the wear characteristics of the plain bearing assembly 126.

The plain bearing assembly 126 comprises a second plain bearing portion 126b. The second plain bearing portion 126b is coupled to the cardiac pump housing 107 such that, during operation of the cardiac pump 101, the second plain bearing portion 126b does not rotate with the cardiac pump rotor 108. In the example shown in FIG. 2b, the second plain bearing portion 126b is integral to the cardiac pump housing 107, although in an alternative example the second plain bearing portion 126b may be a separate component rigidly fixed to the cardiac pump housing 107. In another example, the second plain bearing portion 126b may be movably coupled, for example threadably coupled, to the cardiac pump housing 107 such that the position of the second plain bearing portion 126b may be adjusted relative to the cardiac pump housing 107. The second plain bearing portion 126b may be constructed from a different material to the cardiac pump housing 107, e.g. a ceramic material. Alternatively, the second plain bearing portion 126b may be constructed from a similar material to the cardiac pump housing 107, e.g. a titanium alloy. The second plain bearing portion 126b may comprise a surface coating and/or may have had a surface treatment to improve the wear characteristics of the plain bearing assembly 102. The first and second plain bearing portions 126a, 126b may be constructed from different materials to each other, for example the first and second plain bearing portions 126a, 126b may each be constructed from a different ceramic material.

The first and second plain bearing portions 126a, 126b are configured to engage each other so as to be in contact when the cardiac pump rotor 108 and the cardiac pump housing 107 are in an assembled configuration, such that the plain bearing assembly 126 is configured to rotatably support the cardiac pump rotor 108 within the cardiac pump housing 107. In the example shown in FIG. 2b, the first and second bearing portions 126a, 126b each comprise a substantially planar articular bearing surface arranged perpendicularly to the longitudinal axis A-A. In this manner, the first and second bearing portions 126a, 126b are configured to support the cardiac pump rotor 108 within the cardiac pump housing 107 in an axial direction of the cardiac pump rotor 108.

The first plain bearing portion 126a may comprise a spherical segment, i.e. a truncated spherical cap or spherical frustum. The second plain bearing portion 126b may be substantially disc-shaped. It is appreciated, however, that the first and second bearing portions 126a, 126b may be of any suitable form that permits the plain bearing assembly 126 to support the cardiac pump rotor 108 in at least the axial direction, for example, the first and/or second plain bearing portions 126a, 126b may comprise a frustoconical portion.

In an alternative example, the first and second bearing portions 126a, 126b may be arranged in any suitable manner such that the plain bearing assembly 126 is configured to support the cardiac pump rotor 108 within the cardiac pump housing 107 in at least a radial direction of the cardiac pump rotor 108. As such, the bearing surfaces of the first and second bearing portions 126a, 126b may be of any appropriate form. In one example, plain bearing assembly 126 may be configured to support the cardiac pump rotor 108 in the axial direction and in the radial direction, e.g. the first and second bearing portions 126a, 126b may comprise one or more curved, e.g. partially spherical, or conical bearing surfaces configured to be in rotatable contact. For example, the plain bearing assembly 126 may comprises an at least partial ball and socket bearing, wherein the one or more bearing surfaces of the first and second bearing portions 126a, 126b are substantially conformal. In general, the plain bearing assembly 126 may be configured such that the cardiac pump rotor 108 is substantially constrained in up to five degrees-of-freedom by any combination of point-, line- or surface-contact between the bearing surfaces of the first and second bearing portions 126a, 126b.

The area of contact between the first and second bearing portions 126a, 126b may be optimised with regard to heat generation and wear characteristics of the plain bearing assembly 126. For example, the area of contact may be a substantially circular contact area having an appropriate diameter that may be selected dependent upon operational characteristics of the cardiac pump 101 and the material from which the first and/or second bearing portions 126a, 126b are fabricated. In one example, the substantially circular contact area may have a diameter within a range of approximately 10 µm to 3 mm, or, in particular, within a range of approximately 300 µm to 1 mm. It is appreciated, however, that the shape of the contact area may be of any appropriate form and/or size.

In another example, the plain bearing assembly 126 may comprises a plurality of contact areas, which may each be optimised to provide the desired levels of heat generation and wear characteristics.

The cardiac pump 101 comprises the magnetic bearing assembly 136. The magnetic bearing assembly 136 comprises a first magnetic bearing portion 136a and a second magnetic bearing portion 136b. The first magnetic bearing portion 136a is coupled to the cardiac pump rotor 108 such that, during operation of the cardiac pump 101, the first magnetic bearing portion 136a rotates with the cardiac pump rotor 108. The second magnetic bearing portion 136b is coupled to the cardiac pump housing 107 such that, during operation of the cardiac pump 101, the second magnetic bearing portion 136b does not rotate. The first and/or second magnetic bearing portions 136a, 136b may be rigidly fixed to the cardiac pump rotor 108 and the cardiac pump housing 107 respectively, although in an alternative example the first and/or second magnetic bearing portions 136a, 136b may be movably coupled, for example slidably and/or rotationally coupled, to the cardiac pump rotor 108 and the cardiac pump housing 107 respectively. The position, for example the axial and/or the radial position, of first and/or second magnetic bearing portions 136a, 136b may be adjustable, for example threadably adjustable, relative to the cardiac pump rotor 108 and the cardiac pump housing 107 respectively. It is appreciated, therefore that when the cardiac pump housing 107 and the cardiac pump rotor 108 are in an assembled configuration, the position of the first and/or second magnetic bearing portions 136a, 136b may be adjustable with respect to each other. In this manner, the distance between the first and second magnetic bearing portions 136a, 136b may be adjustable.

The cardiac pump 101 may comprise the further magnetic bearing assembly 156. The further magnetic bearing assembly 156 comprises a first magnetic bearing portion 156a and a second magnetic bearing portion 156b. The first magnetic bearing portion 156a is coupled to the cardiac pump rotor 108 such that, during operation of the cardiac pump 101, the first magnetic bearing portion 156a rotates with the cardiac pump rotor 108. The second magnetic bearing portion 156b is coupled to the cardiac pump housing 107 such that, during operation of the cardiac pump 101, the second magnetic bearing portion 156b does not rotate. The first and/or second magnetic bearing portions 156a, 156b may be rigidly fixed to the cardiac pump rotor 108 and the cardiac pump housing 107 respectively, although in an alternative example the first and/or second magnetic bearing portions 156a, 156b may be movably coupled, for example slidably and/or rotationally coupled, to the cardiac pump rotor 108 and the cardiac pump housing 107 respectively. The position, for example the axial and/or the radial position, of first and/or second magnetic bearing portions 156a, 156b may be adjustable, for example threadably adjustable, relative to the cardiac pump rotor 108 and the cardiac pump housing 107 respectively. It is appreciated, therefore that when the cardiac pump housing 107 and the cardiac pump rotor 108 are in an assembled configuration, the position of the first and/or second magnetic bearing portions 156a, 156b may be adjustable with respect to each other. In this manner, the distance, for example the axial distance, between the first and second magnetic bearing portions 156a, 156b may be adjustable.

The first and/or second magnetic bearing portions 136a, 136b, 156a, 156b may each comprise one or more permanent magnets arranged such that the interaction of the magnetic fields of each of the magnetic bearing assembly 136 and the further magnetic bearing assembly 156 is sufficient to support the cardiac pump rotor 108 within the cardiac pump housing 107. For example, the magnetic bearing assembly 136 and/or the further magnetic bearing assembly 156 may each comprise one or more coaxially and/or concentrically arranged ring magnets, and/or one or more discrete magnets, e.g. discs and/or arcuate segments, circumferentially arranged. In the example shown in FIG. 2b, the first magnetic bearing portions 136a, 156a are radially inner with respect to the second magnetic bearing portions 136b, 156b, respectively. However, in another example, the first magnetic bearing portions 136a, 156a may be radially outer with respect to the second magnetic bearing portions 136b, 156b, respectively.

It is appreciated that the attractive and/or repulsive force between the first and second magnetic bearing portions 136a, 136b of the magnetic bearing assembly 136 and the first and second magnetic bearing portions 156a, 156b of the further magnetic bearing assembly 156 is dependent upon the distance between the respective portions of each of the magnetic bearing assembly 136 and the further magnetic bearing assembly 156. In the example of FIG. 2b, the first and second magnetic bearing portions 136a, 136b of the magnetic bearing assembly 136 are radially further out than the first and second magnetic bearing portions 156a, 156b of the further magnetic bearing assembly 156. The magnetic force, for example magnetic flux density, of the magnetic bearing assembly 136 and the further magnetic bearing assembly 156 may be dependent upon the radial position of each respective magnetic bearing portion 136a, 136b, 156a, 156b. As such, the magnetic bearing assembly 136 and the further magnetic bearing assembly 156 may each be provided at any appropriate radial position depending upon the configuration of the cardiac pump 101. For example, the magnetic bearing assembly 136 may be provided at a first operable radius and the further magnetic bearing assembly 156 may be provided at a second operable radius. The first and second operable radii may be selected depending upon the operational requirements of the respective magnetic bearing assemblies 136, 156.

In the example of FIG. 2b, the first magnetic bearing portion 136a of the magnetic bearing assembly 136 and the first and second magnetic bearing portions 156a, 156b of the further magnetic bearing assembly 156 are rigidly fixed in position, e.g. they are not adjustable. However, the second magnetic bearing portion 136b of the magnetic bearing assembly 136 is axially movable with respect to the first magnetic bearing portion 136a when the cardiac pump rotor 108 and the cardiac pump housing are in an installed configuration.

The magnetic bearing assembly 136 is configured to rotatably support the cardiac pump rotor 108 within the cardiac pump housing 107 in a radial direction of the cardiac pump rotor 108. The magnetic bearing assembly 136 is further configured to bias the cardiac pump rotor 108 within the cardiac pump housing 107 in the axial direction by virtue of an axial offset between the first and/or second magnetic bearing portions 136a, 136b. In the example of FIG. 2b, the second magnetic bearing portion 136b is axially offset, e.g. by a small distance, away from the first magnetic bearing portion 136a. The magnetic bearing assembly 136 is configured, therefore, to provide an axial preload force to preload the plain bearing assembly 126 by virtue of the magnetic forces provided by the axial offset between the respective portions of the magnetic bearing assembly 136.

The further magnetic bearing assembly 156 is configured to rotatably support the cardiac pump rotor 108 within the cardiac pump housing 107 in the radial direction of the cardiac pump rotor 108, i.e. the first and/or second magnetic bearing portions 156a, 156b are substantially axially aligned such that the further magnetic bearing assembly 156 may not exert a further preload force on the plain bearing assembly 126. It is appreciated, however, that the further magnetic bearing assembly 156 may be configured to provide the further preload force in the axial and/or radial directions.

In the example shown in FIG. 2b, the position of the second magnetic bearing portion 136b is axially adjustable relative to the cardiac pump housing 107 by virtue of a threaded engagement of the second magnetic bearing portion 136b and the cardiac pump housing 107. In this manner, the axial position of the second magnetic bearing portion 136b may be adjustably offset from the first magnetic bearing portion 136a. The magnitude of the preload force that the second magnetic bearing portion 136b applies to the plain bearing assembly 126 may be set to a desired level by adjusting the axial position of the second magnetic bearing portion 136b when the cardiac pump housing 107 and the cardiac pump rotor 108 are in an assembled configuration.

The cardiac pump 101 may comprise a magnetic bearing assembly adjuster 176 configured to adjust the position of the first and/or second magnetic bearing portions 136a, 136b of the magnetic bearing assembly 136 and/or first and/or second magnetic bearing portions 156a, 156b of the further magnetic bearing assembly 156. In the example of FIG. 2b, the magnetic bearing assembly adjuster 176 comprises a threaded adjustment mechanism configured to adjust the axial position of the second magnetic bearing portion 136b of the magnetic bearing assembly 136. The cardiac pump housing 107 may comprise a bore having an inner and an outer radial surface.

The inner or the outer surface of the bore may be threaded. The magnetic bearing assembly adjuster 176 may comprise a magnet carrier 178 configured to house the second magnetic bearing portion 136b of the magnetic bearing assembly 136. The magnet carrier 178 may comprise a threaded radial surface configured to engage a corresponding surface of the threaded bore of the cardiac pump housing 107. The magnet carrier 178 may be movably coupled, for example threadably coupled, to the bore of the cardiac pump housing 107 such that the second magnetic bearing portion 136b may be axially positioned by screwing the magnet carrier into or out of the bore. Additionally and/or alternatively, the magnetic bearing assembly adjuster 176 may comprise one or more slidable and/or rotational couplings, for example a cam mechanism, configured to adjust the axial and/or radial position of any of the first and/or second magnetic bearing portions 136a, 136b, 156a, 156b.

The magnet carrier 178 may comprise one or more portions that are configured to engage an adjustment tool. For example, the magnet carrier 178 may comprise one or more recesses and/or projections 180 that are configured to engage an adjustment tool. In one example, the rotational and/or axial position of the magnet carrier 178 may be adjusted by virtue of a magnetic coupling. In such an example, the position of the magnet carrier 178 may be adjusted even when a cover 182 has been placed over the magnetic bearing assembly adjuster 176.

The cardiac pump 101 may comprise an indicator, e.g. an indexed scale, configured to indicate the position of the magnetic bearing assembly adjuster 176, which may for example be configured to indicate the position of the magnet carrier in relation to the cardiac pump housing 107, and thus the position of second magnetic bearing portion 136b in relation to the first magnetic bearing portion 136a. The indexed scale may be calibrated to indicate the amount of preload force.

The magnetic bearing assembly adjuster 176 may comprise a locking mechanism, for example a seconded threaded member configured to lock the position of the magnet carrier in the bore of the cardiac pump housing 107. Additionally and/or alternatively, the magnetic bearing assembly adjuster 176 may be locked in position by virtue of an adhesive and/or by welding the magnet carrier to the cardiac pump housing 107.

The position of the second magnetic bearing portion 136b may be adjusted so that the second magnetic bearing portion 136b is offset from the first magnetic bearing portion 136a in the axial and/or the radial direction depending upon the configuration of the magnetic field of the magnetic bearing assembly 136. In the example shown in FIG. 2b, the second magnetic bearing portion 136b is offset from the first magnetic bearing portion 136a in the axial direction such that the first magnetic bearing portion 136a is closer to the impeller portion 113 of the cardiac pump rotor 108 than the second magnetic bearing portion 136b. In this manner, the magnetic bearing assembly 136 may be configured to bias the cardiac pump rotor 108 towards the plain bearing assembly 126. In the example shown in FIG. 2b, the axial position of the second magnetic bearing portion 136b is adjusted so that the second magnetic bearing portion 136b is axially offset from the first magnetic bearing portion 136a in a direction away from the plain bearing assembly 126. As a result, the magnetic bearing assembly 136 exerts the preload force on the plain bearing assembly 126. In an alternative example, the axial position of the second magnetic bearing portion 136b may be adjusted so that the second magnetic bearing portion 136b is axially offset from the first magnetic bearing portion 136a in a direction towards the plain bearing assembly 126. In another example, however, the second magnetic bearing portion 136b may be offset from the first magnetic bearing portion 136a in the axial and/or radial direction such that the first magnetic bearing portion 136a is further from the impeller portion 113 of the cardiac pump rotor 108 than the second magnetic bearing portion 136b.

The magnitude of the preload force may be set such that the first and second plain bearing portions 126a, 126b are in rotatable contact during normal operational conditions of the cardiac pump 101. During normal operating conditions, the hydraulic forces that act on the cardiac pump rotor 108 may vary during diastole and systole of the left ventricle, and may vary as a result of the desired operational pressure-flow characteristics of the cardiac pump 101. Furthermore, the operational speed of the cardiac pump 101 may be cyclically increased and decreased in order to create a level of pseudo-pulsitility within the systemic cardio vascular system, which may vary the hydraulic loads acting on the cardiac pump rotor 108. It is desirable, therefore, to set the magnitude of the preload force such that these changes in the hydraulic loads on the cardiac pump rotor 108 do not result in an operational clearance between the first and second plain bearing portions 126a, 126b, ensuring that the first and second plain bearing portions 126a, 126b remain in rotatable contact during normal operational conditions of the cardiac pump 101. The magnitude of the preload force may be set so that the first and second plain bearing portions 126a, 126b just remain in rotatable contact at the extremes of a range of hydraulic loads that are experienced under normal operational conditions.

In some circumstances however, the cardiac pump 101 may experience shock loading, for example if the patient trips and falls. Under shock loading, the cardiac pump rotor 108 may be subject to a shock loading force that acts in a direction with at least a component opposite to the direction of the preload force. As the shock loading force may typically be greater than the hydraulic forces experienced by the cardiac pump rotor 108 during normal operation, the shock loading force may cause the cardiac pump rotor to move, for example axially and/or radially, relative to the cardiac pump housing 107 such that there is gap between the first and second plain bearing portions 126a, 126b. The range of movement of the cardiac pump rotor 108 may be limited by the running clearances between the cardiac pump rotor 108 and the cardiac pump housing 107. It is desirable, therefore, to set the position of the second magnetic bearing portion 136b such that the preload force acts on the cardiac pump rotor 108 so as to re-engage the first and second plain bearing portions 126a, 126b at the maximum extent of the range of movement of the cardiac pump rotor 108 following a shock loading event, or indeed any loading condition that acts to move the cardiac pump rotor 108 relative to the cardiac pump housing 107 that disengages the first and second plain bearing portions 126a, 126b.

In the example of FIG. 2b, the cardiac pump rotor 108 comprises a conical surface 114 provided at an opposite end of the cardiac pump 101 to that of the plain bearing assembly 126. The apex of the conical surface is configured to contact the cardiac pump housing 107 such that the maximum extent of the range of movement of the cardiac pump rotor 108 is defined by the distance between the apex of the conical surface and the wall of the cardiac pump housing 107. In this manner, the contact area between the cardiac pump rotor 108 and the cardiac pump housing 107 is minimised upon movement of the cardiac pump rotor 108. It is appreciated, however, that the cardiac pump rotor 108 and/or the cardiac pump housing 107 may comprise any appropriate geometrical features configured to minimise the contact area between the cardiac pump rotor 108 and the cardiac pump housing 107.

The cardiac pump 101 may comprise an optional further plain bearing assembly (not shown) spaced apart from the plain bearing assembly 126 in at least the axial direction. The further plain bearing assembly may be provided at the other end of the cardiac pump rotor 108 to the plain bearing assembly 126. In a similar manner to the plain bearing assembly 126, the further plain bearing assembly may comprise a first plain bearing portion coupled to the cardiac pump rotor 108 and a second plain bearing portion coupled to the cardiac pump housing 107.

The further plain bearing assembly may be configured to limit the range of movement of the cardiac pump rotor 108 within the cardiac pump housing 107, for example in a direction opposite to the direction of the preload force. The cardiac pump may be configured such that during operation, the first and second plain bearing portions 126a, 126b of the plain bearing assembly 126 are in rotatable contact, and the first and second plain bearing portions of the further plain bearing assembly have an operational clearance between each other. The operational clearance may be smaller than the minimum running clearance between the cardiac pump housing 107 and the cardiac pump rotor 108. In this manner, in those circumstances where the cardiac pump rotor 108 moves, for example axially and/or radially, within the cardiac pump housing 107, the first and second plain bearing portions of the further plain bearing assembly are brought into contact before any portion of the cardiac pump rotor 108 contacts the cardiac pump housing 107. In one example, the further plain bearing assembly may comprise first and second plain bearing portions of similar form to the first and second plain bearing portions 126a, 126b of the plain bearing assembly 126, e.g. the first plain bearing portion of the further plain bearing assembly may comprise a spherical segment, i.e. a truncated spherical cap or spherical frustum, and the second plain bearing portion 126 of the further plain bearing assembly may be substantially disc-shaped. It is appreciated, however, that the first and second plain bearing portions of the further plain bearing assembly may be of any appropriate form, and that the first and second plain bearing portions of the further plain bearing assembly may be provided at any location of the cardiac pump rotor 108 and the cardiac pump housing 107 respectively, for example at an opposite end of the cardiac pump 101 to that of the plain bearing assembly 126. The further plain bearing assembly may also comprise the optional features of the plain bearing assembly 126 as described above.

As shown in the example of FIG. 2b, the cardiac pump 101 comprises a magnetic drive coupling 140, for example a brushless DC motor. The cardiac pump rotor 108 comprises a first portion of the magnetic drive coupling 140a, for example one or more permanent magnets. The cardiac pump housing 107 comprises a second portion of the magnetic drive coupling 140b, for example one or more electrical windings. In the example of FIG. 2b, the magnetic drive coupling 140 is a radial magnetic drive coupling, e.g. a radial flux gap electric motor, although it is appreciated that the magnetic drive coupling 140 may be of any appropriate configuration.

The first and second portions of the magnetic drive coupling 140a, 140b may be at least partially disposed in between the magnetic bearing assembly 136 and the further magnetic bearing assembly 156. In the example of FIG. 2b, the first and second portions of the magnetic drive coupling 140a, 140b are disposed axially in between the magnetic bearing assembly 136 and the further magnetic bearing assembly 156, although it is appreciated that the first and second portions of the magnetic drive coupling 140a, 140b may be disposed at any position in between the magnetic bearing assembly 136 and the further magnetic bearing assembly 156, for example radially and/or axially in between the magnetic bearing assembly 136 and the further magnetic bearing assembly 156.

The cardiac pump rotor 108 is coupled to the impeller portion 113, which may be provided at an end of the cardiac pump rotor 108. In the example of FIG. 2b, the impeller portion 113 comprises a radial-flow impeller, although in an alternative example, the impeller portion may comprise an axial-flow impeller or a mixed-flow impeller. The impeller portion 113 may be at least partially disposed in between the magnetic bearing assembly 136 and the further magnetic bearing assembly 156. In the example of FIG. 2b, the impeller portion 113 is disposed axially in between the magnetic bearing assembly 136 and the further magnetic bearing assembly 156, although it is appreciated that the impeller portion 109 may be disposed at any position in between the magnetic bearing assembly 136 and the further magnetic bearing assembly 156, for example radially and/or axially in between the magnetic bearing assembly 136 and the further magnetic bearing assembly 156. In the example shown in FIG. 2b, the impeller portion 113 is provided in between the magnetic bearing assembly 136 and the magnetic drive coupling 140, although in an alternative example the impeller portion 113 may be provided in between the further magnetic bearing assembly 156 and the magnetic drive coupling 140.

In the example of FIG. 2b, the cardiac pump 101 comprises the magnetic bearing assembly 136, which is configured to support radially one end of the cardiac pump rotor 108, and the further magnetic bearing assembly 156, which is configured to support radially the other end of the cardiac pump rotor 108. The magnetic drive coupling 140 and the impeller portion 113 are disposed in between the magnetic bearing assembly 136 and the further magnetic bearing assembly 156. In the example shown in FIG. 2b, the impeller portion 113 is provided axially in between the magnetic bearing assembly 136 and the magnetic drive coupling 140, and the magnetic drive coupling 140 is provided axially in between the impeller portion 113 and the further magnetic bearing assembly 156. In this manner, the centre of mass of the cardiac pump rotor 108 is located in between the magnetic bearing assembly 136 and the further magnetic bearing assembly 156, and the mass of the cardiac pump rotor 108 that overhangs either of the magnetic bearing assembly 136 and the further magnetic bearing assembly 156 may be minimised. Furthermore any forces that act on the cardiac pump rotor 108, for example axial and/or radial loading as a result of the electromagnetic forces of the magnetic drive coupling 140 and/or hydraulic forces acting on the impeller portion 113, act on a portion of the cardiac pump rotor 108 in between the magnetic bearing assembly 136 and the further magnetic bearing assembly 156. This improves the stability of the cardiac pump rotor 108 during operation of the cardiac pump 101.

In the example shown in FIG. 2b, the first magnetic bearing portion 136a of the magnetic bearing assembly 136 is provided in a shaft portion 157 of the cardiac pump rotor 108 that extends axially from the impeller portion 113. In this manner, the magnetic bearing assembly 136 may be offset from the impeller portion 113 by an offset distance D1. In FIG. 2b, the offset distance D1 is shown as the distance between an impeller shroud 119 and an edge of the first magnetic bearing portion 136a closest to the impeller shroud 119. The offset distance D1 may, however, be measured between any appropriate portions of the impeller portion 113 and the magnetic bearing portion 136a respectively.

During operation of the cardiac pump 101, the hydraulic forces acting upon the impeller portion 113 may cause a hydraulic moment to be applied to the cardiac pump rotor 108 that acts to tilt the cardiac pump rotor 108 off its rotational axis. The position of the magnetic bearing assembly 136, for example the offset distance D1 between the magnetic bearing assembly 136 and the impeller portion 113, may be selected depending upon the magnitude of the hydraulic forces, and thus the magnitude of the hydraulic moment, acting on the cardiac pump rotor 108. For example, the magnetic bearing assembly 136 may be configured to counteract the hydraulic moment by virtue of a magnetic force that is applied to the cardiac pump rotor 108 when the cardiac pump rotor 108 is tilted off its rotational axis. The offset distance D1 may determine the magnitude of a magnetic moment that counteracts the hydraulic moment.

In a similar manner, the position of the further magnetic bearing assembly 156, for example the offset distance D2 between the further magnetic bearing assembly 156 and the impeller portion 113, may be selected depending upon the magnitude of the hydraulic forces acting on the impeller portion 113.

Additionally or alternatively, the offset distances D1, D2 may be selected depending on the magnitude of an electromagnetic moment that acts to tilt the cardiac pump rotor 108 off its rotational axis caused by the electromagnetic forces acting on the cardiac pump rotor 108 as a result of the operation of the magnetic drive coupling 140. The offset distances may be selected to optimise the rotational stability of the cardiac pump rotor 108 during operation of the cardiac pump 101.

Figure 3:
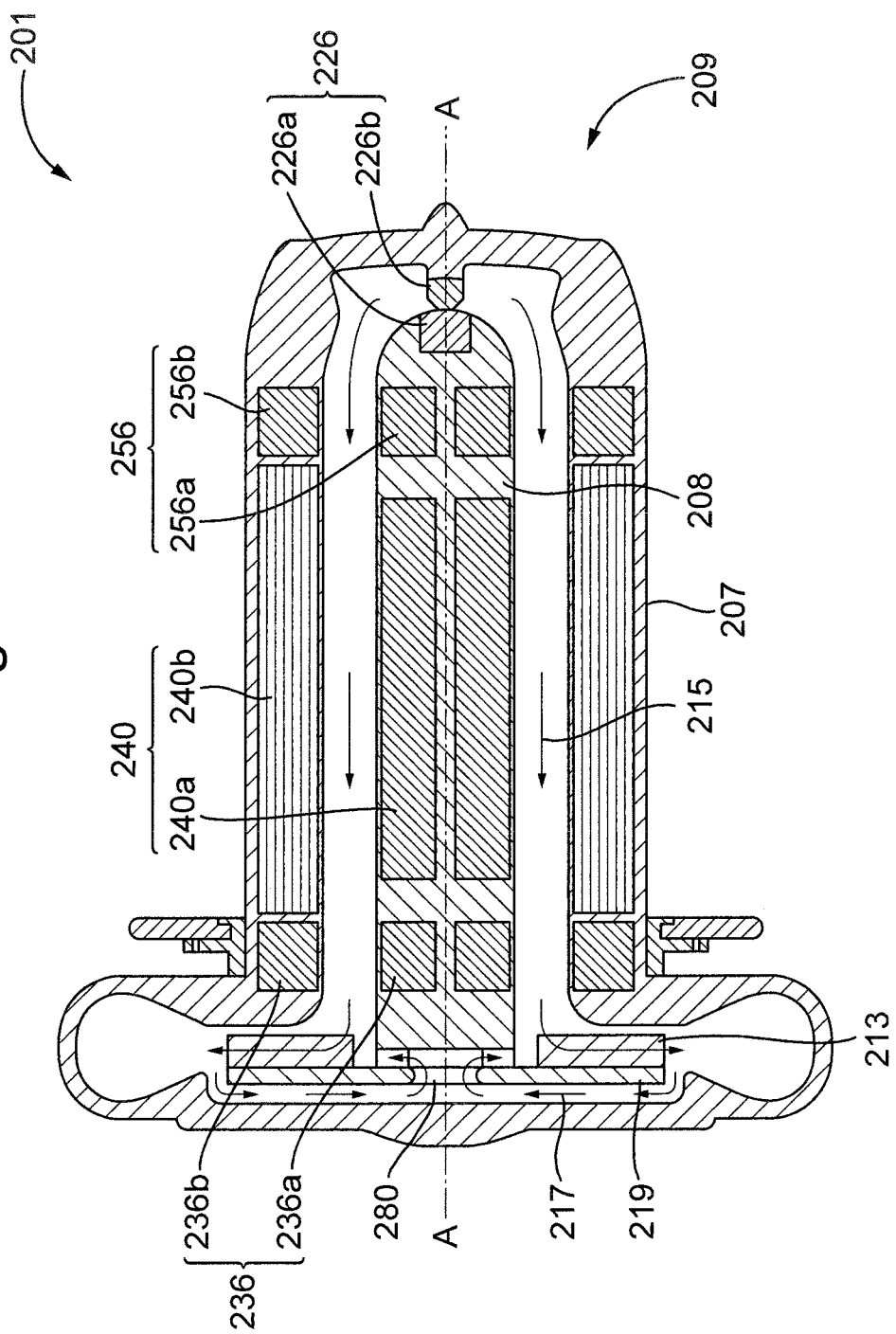
FIG. 3 shows a cross sectional view of another example of a cardiac pump according to the present disclosure in an assembled configuration.

It is appreciated however that the present disclosure is not limited to the layout as shown in FIG. 2b. FIG. 3 shows an alternative example of the cardiac pump 201, in which the magnetic drive coupling 240 is disposed in between the magnetic bearing assembly 236 and the further magnetic bearing assembly 256, and the impeller portion 213 is disposed towards the end of the cardiac pump rotor 208 outside of the magnetic bearing assembly 236 and the further magnetic bearing assembly 256, for example such that the impeller portion 213 is not in between the magnetic bearing assembly 236 and the further magnetic bearing assembly 256.

Figure 4:
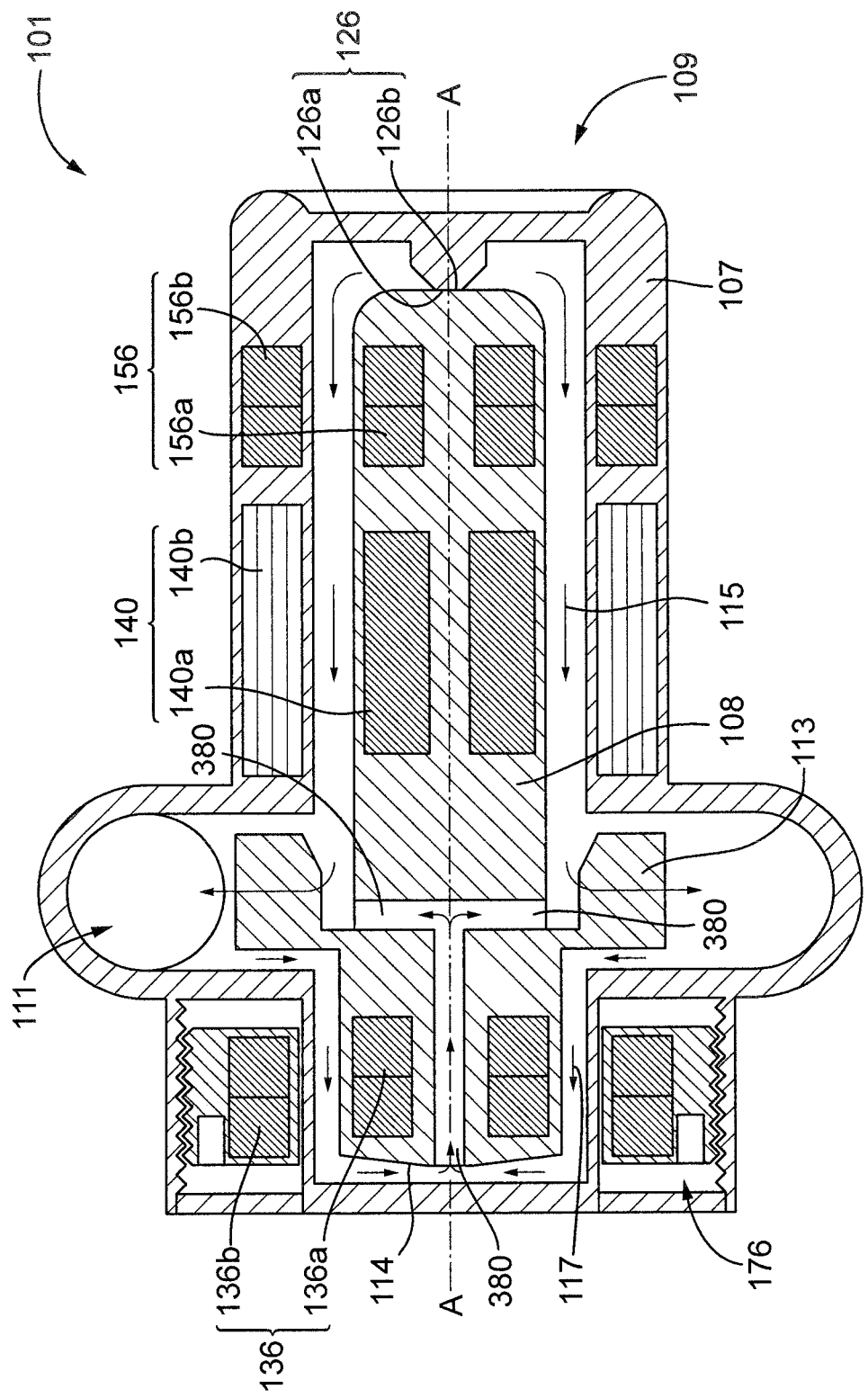
FIG. 4 shows a cross sectional view of a further example of a cardiac pump according to the present disclosure in an assembled configuration

FIG. 4 shows a modified example of the cardiac pump 101 shown in FIG. 2. In the examples shown in FIGS. 3 and 4, the cardiac pump rotor 208, 108 comprises one or more flow channels 280, 380 that extend through the cardiac pump rotor 208, 108. The flow channels 280, 380 may be configured to connect two or more regions of the primary flow 215, 115 to one another and/or fluidically connect a region of the secondary flow 217, 117 to a region of the primary flow 215, 115. In the example shown in FIG. 3, the flow channels 280 extend through the impeller portion 213 of the cardiac pump rotor 208, and in the example shown in FIG. 4, the flow channels 380 extend through the shaft portion 157 and the impeller portion 113 of the cardiac pump rotor 108. In this manner, blood flows from a high pressure region at an outer diameter of the impeller portion 213, 113 towards a lower pressure region at in inner diameter of the impeller portion 213, 113, thereby defining the secondary flow path 217, 117. In this manner, the secondary flow 217, 117 may act to disrupt any areas of flow stasis that may exist between an impeller shroud 219, 119 of the impeller portion 213, 113 and the cardiac pump casing 207, 107. The present disclosure, therefore, may serve to mitigate the predilection for areas of flow stasis that may be associated with deposition of proteins and/or thrombus formation, thus reducing the overall number of adverse events due to bearing malfunction and/or failure in implanted devices. Although not shown in FIG. 2a, FIG. 2b, FIG. 3 or FIG. 4, it is appreciated that the plain bearing assembly 126, 226 and/or the further plain bearing assembly may be located in the secondary flow path 217, 117.

The present disclosure provides a method of preloading the plain bearing assembly 126, 226 with a preload force provided by the magnetic bearing assembly 136, 236. The present disclosure further provides a method of setting the preload force by adjusting the position of the position of the first and/or the second magnetic bearing portion 136a, 136b, 236a, 236b relative to the cardiac pump rotor 108, 208 and/or the cardiac pump housing 107, 207 when the cardiac pump housing 107, 207 and the cardiac pump rotor 108, 208 are in an assembled configuration. Furthermore, larger manufacturing tolerances may be permitted by virtue of the adjustability of the magnetic bearing assembly 136, 236 for example the adjustability of the position of the first and/or the second magnetic bearing portion 136a, 136b, 236a, 236b.

It may be generally appreciated that the described examples of the plain bearing assembly 126, 226 and magnetic bearing assembly 136, 236 may not be confined to use with their associated examples of the cardiac pump 101, 201. Indeed, each of the described plain bearing assembly 126, 226 and magnetic bearing assembly 136, 236 in accordance with the present invention may be installed in any of the described examples or any other appropriate cardiac pump.

The invention claimed is:

1. A cardiac pump comprising:
a plain bearing assembly comprising a first plain bearing portion and a second plain bearing portion, the first plain bearing portion being coupled to a cardiac pump rotor and the second plain bearing portion being coupled to a cardiac pump housing, the plain bearing assembly being configured to rotatably support the cardiac pump rotor within the cardiac pump housing in at least an axial direction of the cardiac pump rotor; and
a magnetic bearing assembly comprising a first magnetic bearing portion and a second magnetic bearing portion, the first magnetic bearing portion being coupled to the cardiac pump rotor and the second magnetic bearing portion being coupled to the cardiac pump housing, the magnetic bearing assembly being configured to rotatably support the cardiac pump rotor within the cardiac pump housing in a radial direction of the cardiac pump rotor and bias the cardiac pump rotor in the axial direction such that the magnetic bearing assembly provides a preload force to preload the plain bearing assembly; wherein at least one of:

(1) the position of the first and/or second magnetic bearing portion is adjustable relative to the cardiac pump rotor and/or the cardiac pump housing when the cardiac pump housing and the cardiac pump rotor are in an assembled configuration, such that the magnitude of the preload force is dependent upon the position of the first and/or second magnetic bearing portion; and
(2) the position of the first and/or second plain bearing portion is adjustable relative to the cardiac pump rotor and/or the cardiac pump housing such that the magnitude of the preload force is dependent upon the position of the first and/or second plain bearing portion when the cardiac pump housing and the cardiac pump rotor are in an assembled configuration; and
(3) the cardiac pump further comprises a magnetic bearing assembly adjuster configured to adjust the position of the first and/or second magnetic bearing portion; and
(4) the cardiac pump further comprises a further magnetic bearing assembly, the magnetic bearing assembly and the further magnetic bearing assembly being spaced apart from each other in at least the axial direction; and
(5) the plain bearing assembly is further configured to support the cardiac pump rotor in the radial direction; and
(6) the cardiac pump further comprises a further plain bearing assembly, the plain bearing assembly and the further plain bearing assembly being spaced apart from each other in at least the axial direction.

2. A cardiac pump according to claim 1, wherein the position of the first and/or second magnetic bearing portion is adjustable relative to the cardiac pump rotor and/or the cardiac pump housing when the cardiac pump housing and the cardiac pump rotor are in an assembled configuration, such that the magnitude of the preload force is dependent upon the position of the first and/or second magnetic bearing portion.

3. A cardiac pump according to claim 2, wherein the position of the second magnetic bearing portion is adjustable relative to the cardiac pump rotor and/or the cardiac pump housing when the cardiac pump is in an operable configuration, such that the magnitude of the preload force is dependent upon the position of the second magnetic bearing portion.

4. A cardiac pump according to claim 2, wherein the first and/or second magnetic bearing portion is threadably adjustable.

5. A cardiac pump according to claim 2, wherein the position of the first and/or the second magnetic bearing portion is adjustable in the axial and/or the radial direction.

6. A cardiac pump according to claim 1, wherein the position of the first and/or second plain bearing portion is adjustable relative to the cardiac pump rotor and/or the cardiac pump housing such that the magnitude of the preload force is dependent upon the position of the first and/or second plain bearing portion when the cardiac pump housing and the cardiac pump rotor are in an assembled configuration.

7. A cardiac pump according to claim 1, wherein the cardiac pump further comprises a magnetic bearing assembly adjuster configured to adjust the position of the first and/or second magnetic bearing portion.

8. A cardiac pump according to claim 1, wherein the cardiac pump comprises a further magnetic bearing assembly, the magnetic bearing assembly and the further magnetic bearing assembly being spaced apart from each other in at least the axial direction.

9. A cardiac pump according to claim 8, wherein the further magnetic bearing assembly is configured to at least partially support the cardiac pump rotor within the cardiac pump housing in the axial direction and/or the radial direction.

10. A cardiac pump according to claim 8, wherein the further magnetic bearing assembly is configured to bias the cardiac pump rotor in the axial direction and/or the radial direction.

11. A cardiac pump according to claim 8, wherein the cardiac pump rotor comprises a first portion of a magnetic drive coupling and the cardiac pump housing comprises a second portion of the magnetic drive coupling, wherein the first and second portions of the magnetic drive coupling are at least partially disposed in between the magnetic bearing assembly and the further magnetic bearing assembly.

12. A cardiac pump according to claim 8, wherein the cardiac pump rotor comprises an impeller portion, the impeller portion being at least partially disposed in between the magnetic bearing assembly and the further magnetic bearing assembly.

13. A cardiac pump according to claim 1, wherein the plain bearing assembly is further configured to support the cardiac pump rotor in the radial direction.

14. A cardiac pump according to claim 1, wherein the cardiac pump comprises a further plain bearing assembly, the plain bearing assembly and the further plain bearing assembly being spaced apart from each other in at least the axial direction.

15. A cardiac pump according to claim 14, wherein the further plain bearing assembly is configured to limit a range of movement of the cardiac pump rotor within the cardiac pump housing in a direction opposite to the direction of the preload force.

16. A cardiac pump according to claim 14, wherein the cardiac pump is configured such that during operation the first and second plain bearing portions of the plain bearing assembly are in rotatable contact, and the first and second plain bearing portions of the further plain bearing assembly have an operational clearance between each other.

17. A cardiac pump according to claim 14, wherein the cardiac pump further comprises a primary flow path configured to connect fluidically a cardiac pump inlet and a cardiac pump outlet, and one or more secondary flow paths, the secondary flow paths being at least partially configured to connect fluidically two or more regions of the primary flow path.

18. A cardiac pump according to claim 17, wherein the plain bearing assembly is at least partially disposed within the primary flow path.

19. A cardiac pump according to claim 17, wherein the further plain bearing assembly is at least partially disposed within the secondary flow path.

20. A cardiac pump according to claim 19, wherein the cardiac pump is configured such that during operation the operational clearance between the first and second plain bearing portions of the further plain bearing assembly is at least partially disposed in the secondary flow path.

21. A method of preloading a plain bearing assembly of a cardiac pump, the cardiac pump comprising the plain bearing assembly and a magnetic bearing assembly, wherein:

the plain bearing assembly comprises a first plain bearing portion and a second plain bearing portion, the first plain bearing portion being coupled to a cardiac pump rotor and the second plain bearing portion being coupled to a cardiac pump housing, the plain bearing assembly being configured to rotatably support the cardiac pump rotor within the cardiac pump housing in at least an axial direction of the cardiac pump rotor, and the magnetic bearing assembly comprises a first magnetic bearing portion and a second magnetic bearing portion, the first magnetic bearing portion being coupled to the cardiac pump rotor and a second magnetic bearing portion being movably coupled to the cardiac pump housing, the magnetic bearing assembly being configured to rotatably support the cardiac pump rotor within the cardiac pump housing in a radial direction of the cardiac pump rotor and bias the cardiac pump rotor in the axial direction such that the magnetic bearing assembly provides a preload force to preload the plain bearing assembly when the cardiac pump housing and the cardiac pump rotor are in an assembled configuration, the method comprising the step of preloading the plain bearing assembly with the preload force provided by the magnetic bearing assembly, wherein the magnitude of the preload force is dependent upon the position of the first and/or the second magnetic bearing portion, the method further comprising adjusting the position of the first and/or the second magnetic bearing portion relative to the cardiac pump rotor and/or the cardiac pump housing when the cardiac pump housing and the cardiac pump rotor are in an assembled configuration.

* * * * *